(12) United States Patent
Fasoli et al.

(10) Patent No.: US 11,298,091 B2
(45) Date of Patent: Apr. 12, 2022

(54) DEVICE FOR POSITIONING A PATIENT DURING ACQUISITION OF VOLUMETRIC CBCT RADIOGRAPHS

(71) Applicant: CEFLA Societá Cooperativa, Imola (IT)

(72) Inventors: Martino Fasoli, Imola (IT); Jacopo Molinaroli, Imola (IT); Simone Chiampan, Imola (IT)

(*) Notice: Subject to any disclaimer, the term of this patent is extended or adjusted under 35 U.S.C. 154(b) by 0 days.

(21) Appl. No.: 16/948,028

(22) Filed: Aug. 27, 2020

(65) Prior Publication Data
US 2021/0059618 A1    Mar. 4, 2021

(30) Foreign Application Priority Data

Sep. 2, 2019  (IT) .................. 202019000002910
Sep. 2, 2019  (IT) .................. 202019000002913

(51) Int. Cl.
| | |
|---|---|
| *A61B 6/04* | (2006.01) |
| *A61B 6/03* | (2006.01) |
| *A61B 6/14* | (2006.01) |
| *A61B 6/08* | (2006.01) |
| *A61B 6/00* | (2006.01) |

(52) U.S. Cl.
CPC .......... *A61B 6/0421* (2013.01); *A61B 6/035* (2013.01); *A61B 6/0487* (2020.08); *A61B 6/08* (2013.01); *A61B 6/14* (2013.01); *A61B 6/4435* (2013.01); *A61B 6/5241* (2013.01)

(58) Field of Classification Search
CPC .......... A61B 6/037; A61B 6/032; A61B 6/04; A61B 6/0407; A61B 10/0233; A61B 6/4233; A61B 6/4435; A61B 6/4085; A61B 6/4405; A61B 6/501; A61B 5/6891; A61N 5/10; A61N 2005/1063; A61N 2005/1097; A61G 2203/36
See application file for complete search history.

(56) References Cited

U.S. PATENT DOCUMENTS

2011/0145991 A1*  6/2011  Bridge .................. A61G 7/103
                                                    5/601

\* cited by examiner

*Primary Examiner* — Don K Wong
(74) *Attorney, Agent, or Firm* — Themis Law (57) ABSTRACT

A radiographic apparatus includes a gantry and a table supporting a patient and having a device that immobilizes the head of the patient lying on the table. Such device includes a dome configured to support the head of the patient; a basal plate; one or more junctions provided at a first end of the basal plate; two uprights provided at a second end of the basal plate opposed to the first end, two slits being defined in the two uprights, a slide being disposed within each slit; and a cursor sliding in the two slits and configured to be blocked in position by a bushing, wherein the basal plate, the one or more junctions, the two uprights, the cursor, and the bushing are all radio-transparent and non-metallic.

15 Claims, 8 Drawing Sheets

DEVICE FOR POSITIONING A PATIENT DURING ACQUISITION OF VOLUMETRIC CBCT RADIOGRAPHS

FIELD OF THE INVENTION

The present invention relates to an extraoral radiographic apparatus, allowing to acquire volumetric 3D images. In particular, the invention relates to a radio-transparent device for immobilizing a patient's head, capable of blocking her/his head without oppressing the patient.

In particular, the invention relates further to a combination between a patient table capable of movement along the three space axes and an X-ray sensor having reduced dimensions, which as it will be apparent from the following, provides further advantages in combination with a device for immobilizing the patient's head.

In particular, the present invention finds advantageous, but not exclusive, application in computerized tomography scanners used in the sector of dentistry, to which the ensuing description will make explicit reference, without this implying any loss of generality.

BACKGROUND OF THE INVENTION

Computerized tomography scanners provided with a through gantry hosting a lying patient, used in dental practice and hospitals, are of the type comprising a frame supporting a gurney, in its turn supporting a lying patient, and an X-ray source-detector assembly. Said assembly is designed to rotate about an anatomical area of analysis for acquiring raw volumetric tomographic data of a particular anatomical area of interest of the patient, e.g. head, limbs, or portions of the vertebral column.

Preferably, but not necessarily, the radiographic technology is cone-beam volumetric radiography (also known as CBCT or 3D), i.e. the acquisition from different projection angles, of a series of two-dimensional radiographic images, which will be processed post-acquisition to reconstruct three-dimensional volumes.

The tomography scanner further comprises a control unit, connected to the source-detector assembly, for controlling the emission and reception of the X-ray beam in a way synchronous with the rotation of the X-ray source and detector, and a processing unit connected to the detector for receiving, storing, and processing the volumetric tomographic data so as to reconstruct images of the object. The processing unit is provided with a screen in order to allow the visualization of the reconstructed images.

As anticipated, typically the apparatus comprises a table on which a patient lies to acquire images, and a gantry hosting the X-ray source-detector (or sensor) assembly. The patient's table is provided with a gurney which can slide inside and outside from the gantry, so as to acquire different anatomical areas of a patient. Typically, the patient lies down on the table gurney while the gurney is in its extracted position with respect to the gantry. After this, the gurney is raised/lowered or laterally displaced so as to bring it in correspondence to the gantry hole, and then the gurney is slid inside the gantry up to a position suitable for acquiring the specific radiographic image; then the image acquisition can start. The acquisition takes place while the X-ray source and detector rotate around the patient. Once the acquisition is completed, the gurney is extracted from the gantry and the patient can stand up for releasing.

In the art, providing relocatable supports for the patient's head is known. Such relocatable supports can be fixed to the table supporting the patient.

U.S. Ser. No. 10/272,008B2 in the name of Neural Analytics Inc. describes a device for positioning the head of a patient lying on a table. Said device can be positioned on a tilted table, but cannot be tilted as such. The device is suitable for being positioned on a patient's table provided with a continuous tilting, ranging 0 to 45°. Patient's head is blocked by Velcro bands and soft wedges.

In the art, it is known that the anatomical portion to be acquired must be blocked in order to prevent the generation of motion artefacts. Therefore, there is the need to build a support structure as rigid as possible. On the other hand, as the support structure is inside the field of view (FOV), and therefore is impinged upon by X-rays, it must be built in materials that are as radio-transparent as possible (e.g. plastic materials, carbon, etc.). At the same time, the presence of metallic materials must be kept to a minimum, in that metal generates different artefacts, significantly altering the acquired radiographic image.

Moreover, keeping to a minimum the presence of any non-anatomical object placed inside the field of view reduces the possibility of reading errors of the radiograph by the radiologist.

In the art, it is known that there are provided organs that are especially sensitive to radiation damage, like e.g. eyes, pituitary gland, thyroid, genital organs.

Finally, there must be provided a head support that can be used for otolaryngological acquisitions, in particular patient's ears, which are a particularly critical area, in that in their immediate surroundings there are provided particularly sensitive glands and organs, like some of the above-quoted ones.

U.S. Ser. No. 06/619,839 in the name of Morita describes an extraoral radiographic apparatus wherein the patient support is provided in the form of a chair. Said chair is a positioning device of an object to be radiographed. The apparatus comprises moving means aimed at moving the object to be radiographed along the three space axes with respect to the rigid X-ray source-detector system, in order to acquire at least a scout image.

EP1972277A1 by the same applicant describes an extraoral radiographic apparatus provided with a table on which a patient is lying. In this case, too, the apparatus is provided with moving means aiming at moving the object to be acquired along the three space axes with respect to the rigid X-ray source-detector system according to the acquisition of at least a scout image.

Providing arrangements that allow for a precise displacement of the patient within the gantry and in relation to the scanning units is important, particularly when the position of the patient is blocked by devices combined with the gurney or other patient supporting devices. In this condition, the patient cannot move for changing her/his position when the FOV is not correctly centered with the scanning unit. In order to relocate the patient for example in relation to a lateral change in position, in the presence of a device blocking the position of the patient, the locked condition must be removed for allowing the patient to correctly reposition. Furthermore, it has to be noticed that acquiring a scout image when using radiographic devices is connected with delivering a dose to the patient, although reduced one, relatively to the full imaging dose of radiation. Nevertheless, the correct positioning of the patient can be determined only by acquiring a scout image and thus by transmitting the corresponding dose to the patient.

Each repositioning procedure of the patient is thus time consuming and needs to be verified by acquiring an image and thus delivering radiation to the patient.

A further drawback of the known art is that the most expensive component of an extraoral radiographic apparatus is the X-ray sensor panel. The bigger the panel, the higher its cost.

Therefore, the focused volume (Field of View, FOV) being equal, the smaller the panel, the cheaper the overall cost of the radiographic apparatus is.

SUMMARY OF THE INVENTION

An aim of the present invention is providing a support for a patient's head, capable of blocking her/his head in the positions needed for the different kinds of acquisitions, suitable for generating no artefacts, either motion artefacts or metal artefacts.

This object is achieved by an apparatus and a method having the features described hereinafter. Advantageous embodiments and refinements are also described hereinafter.

In particular, the present invention provides a relocatable headrest that can be fixed/removed to/from the table gurney provided for patients. Said headrest is provided with different tilting degrees, in order to block patient's head with the tilting needed for the specific image to be acquired.

A first advantage of the present headrest according to the present invention is providing a radio-transparent totally free from metal components in the frame of said headrest, its mechanism of insertion and tilting, as well as of the gurney on which the insertion of said headrest takes place.

A second advantage is in providing an area to be irradiated that is free of support components, as the geometry of the device provides that the supporting elements are as much as possible outside the field of view.

A third advantage of the present invention is the possibility of tilting up to 45° the skull cap, so that ears can be irradiated (otolaryngological use). This without impinging on eyes, thyroid, pituitary gland and other glands which determine a high contribution to the effective dose, i.e. to the weighted sum of the equivalent doses to various organs and tissues (minimization of the irradiation effect).

A fourth advantage of the present invention is the rapidity with which a human operator can insert or remove the headrest according to the present invention to the table gurney, as the radiographic apparatus can be used to acquire patient's anatomic portions other than her/his head.

A further aim of the present invention is providing an extraoral radiographic apparatus with an improved patient positioning arrangement, which allows to avoid a repeated locking and unlocking of the patient to a lock device.

Still a further aim of the present invention is to provide an extraoral radiographic apparatus with a low price thanks to the use of a smaller X-ray sensor panel. Said smaller dimensions are made possible by the movement of the patient support along the three space axes.

This object is achieved by an apparatus and a method having the features of the dependent claims.

In particular, the present invention is provided with a patient bed and a gantry provided with a 30×30 cm sensor panel which, in combination with the movement along the three space axes of the patient support, allows to acquire FOVs having a diameter D up to 30 cm×lengths variable between 5 cm up to the entire vertebral column by using multiple acquisitions. Overall, the table gurney can be moved along its longitudinal axis of 150 cm, while laterally it can be moved up to 21 cm. The gurney is provided with a vertical stroke of about 40 cm.

A first advantage of the combination sensor panel-patient table mobile along the three space axes according to the present invention consists in reducing the cost of the apparatus: in that in this way, the same anatomic portions can be acquired using a much smaller sensor panel. For a comparison, in order to acquire images like those acquired through the present invention, but using a patient support unable to move laterally, a sensor panel capable of acquiring a FOV of at least 50 cm should be used, with an exponential increase of the cost of the sensor panel, and therefore of the radiographic apparatus.

A second advantage consists in a better centering of the anatomic volumes, and therefore in irradiating smaller anatomic portions, preventing a needless biologic damage to patients.

BRIEF DESCRIPTION OF THE DRAWINGS

Further advantages and properties of the present invention are disclosed in the following description, in which exemplary embodiments of the present invention are explained in detail based on the drawings.

DETAILED DESCRIPTION OF EMBODIMENTS OF THE INVENTION

Figure 1:
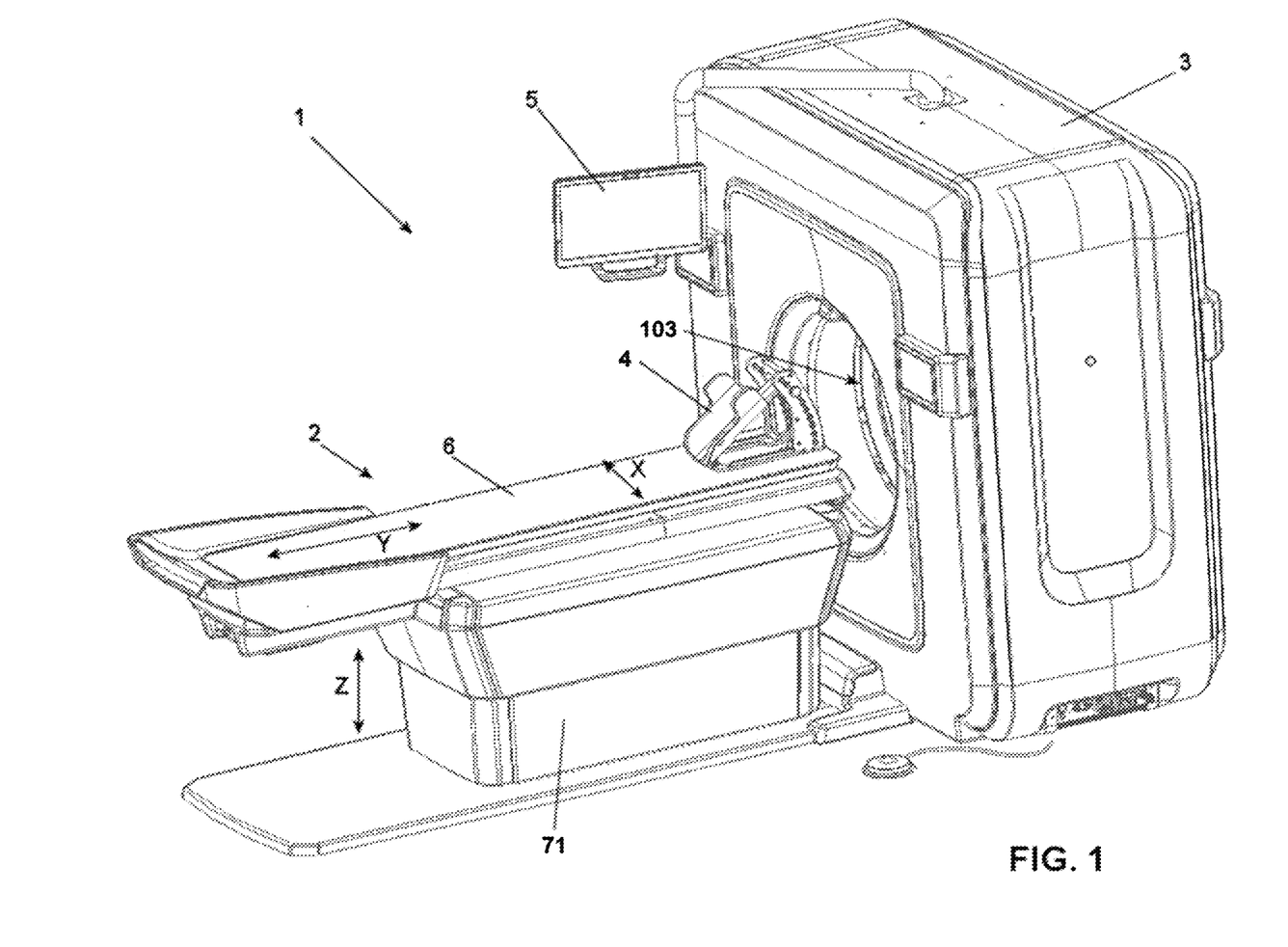
FIG. 1 is an axonometric view of a radiographic apparatus according to the present invention, with the gurney in its extracted position (first extreme position)

FIG. 1 shows an extraoral radiographic apparatus 1, comprising a table 2 for positioning a (not shown) patient in a lying position, and a gantry 3, in its turn comprising a not shown X-ray source and detector.

Said table 2 comprises a relocatable, adjustable device 4 for immobilizing patient's head.

Said apparatus 1 comprises a screen 5 to visualize the images of the patient, or an instruction panel.

Figure 2:
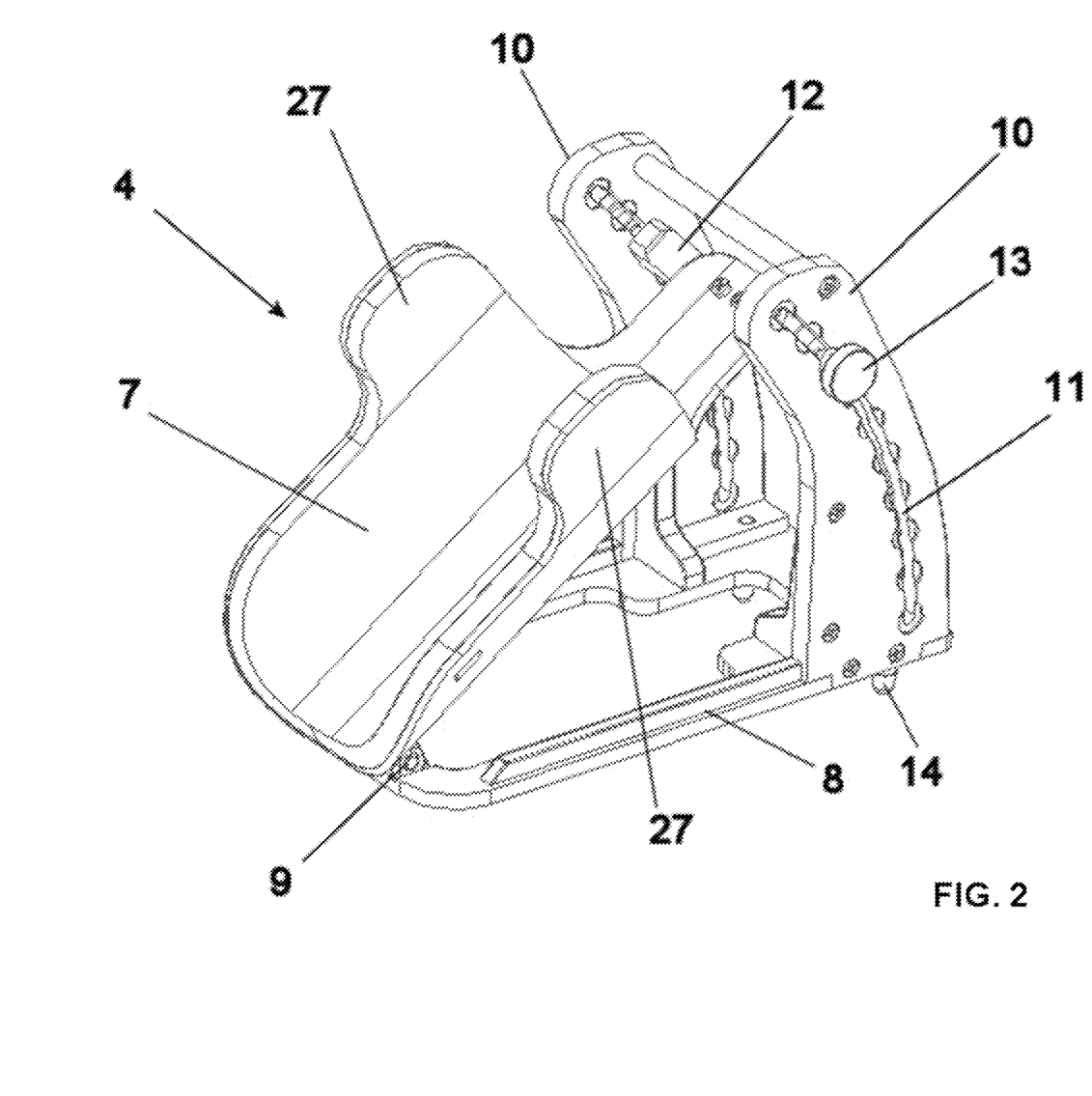
FIG. 2 is an axonometric view of a detail of the headrest.

FIG. 2 shows a detail of the device 4 for immobilizing the head of a not shown patient. Said device 4 is provided with a headrest dome 7, tilting from a first extreme planar position that is parallel to the plane of the gurney 6 and adjacent to it (visible in FIG. 4), to a tilted position which can reach up to 45° in its second extreme position. Said dome 7 can be blocked in intermediate positions between 0° and 45°.

Said dome 7 is provided with the shape of a cradle, consisting in a plane having ends raised with respect to said plane. In its distal portion, nearer to uprights 10, said dome is provided with two protuberances 27 protruding from the border of said plane, aiming at further holding patient's head.

Said device 4 for immobilizing patient's head comprises a basal plate 8, made of radio-transparent material and hollowed out, which is in contact with said gurney 6. Partially said plate 8 can be focused inside the FOV.

On said plate 8, on the side opposed to the gantry 3, there are provided two junctions 9 made of radio-transparent material, allowing a tilting movement of the dome 7.

At the end opposed to the junctions 9 (i.e. oriented toward said gantry 3), on the plate 8 there are provided two uprights 10, which are radio-transparent, too. Said uprights have a guiding function, while at the same time create a rigid structural element aiming at correctly immobilizing the head of the patient. Said two uprights 10 are placed so as not to be irradiated, in order to generate no artefact. Each upright 10 comprises a slit 11, inside which a cursor 12 slides, which is fixed to the end of said dome 7. The cursor 12 can be blocked in pre-set positions through a radio-transparent nut 13. E.g. the device 4 is provided with a blocked position every e.g. 5° of tilting.

In an alternative embodiment, the fixing of the dome 7 on the uprights 10 is continuous, without pre-set positions.

Figure 3:
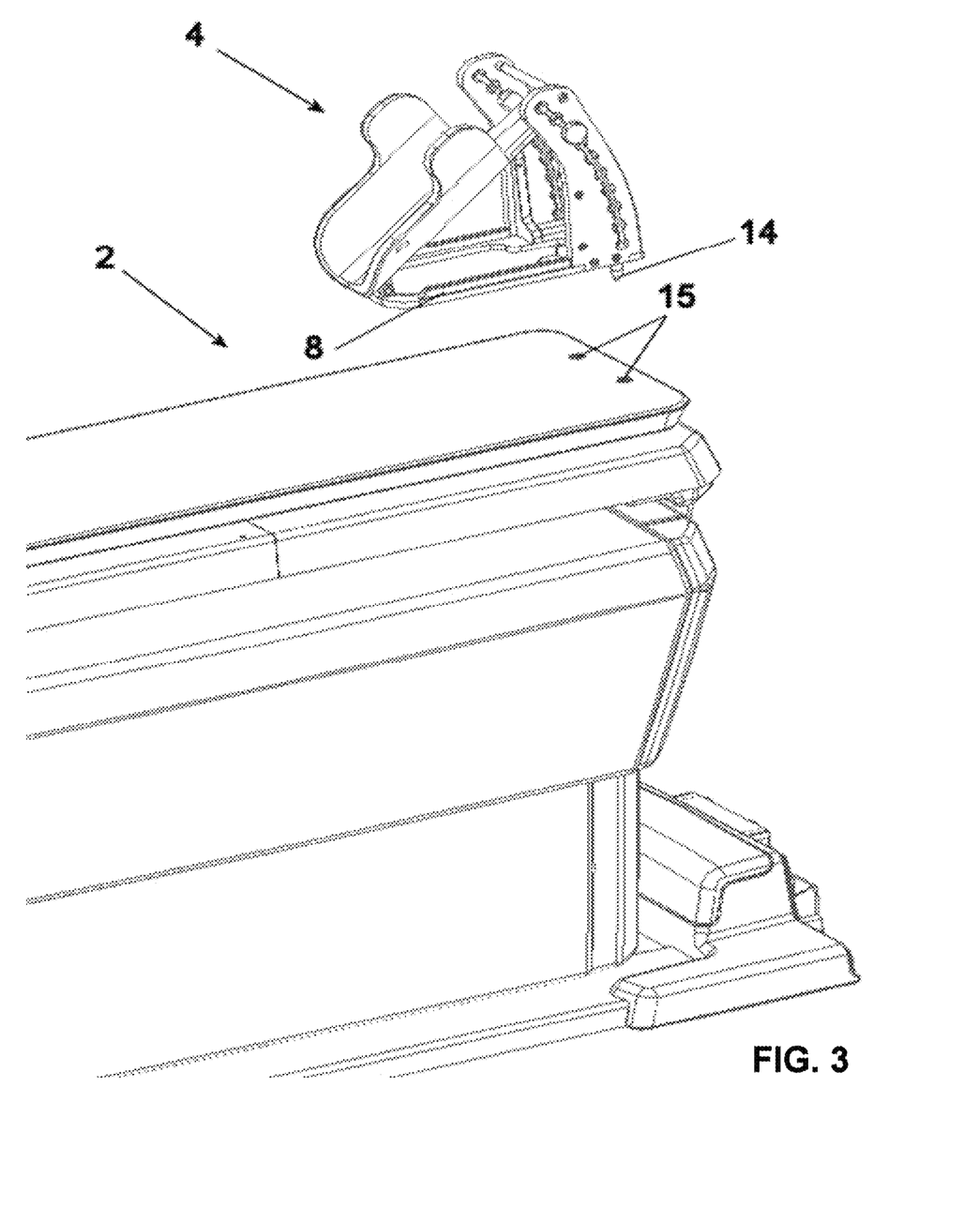
FIG. 3 is an axonometric view of the detail of the fixing of the headrest to the gurney.

FIG. 3 shows a detail of the fixing system of said device 4. Said system comprises two centering pins 14 placed in the lower portion of the plate 8, at the opposed end of the junctions 9 of said plate, under said uprights 10. Due to the image prospective, only a pin 14 is visible in FIG. 3.

The fixing system further comprises two radio-transparent bushing 15, which are inserted at the end of the gurney 6 oriented toward said gantry 3. Obviously, said two pins 14 and bushing 15 are placed in corresponding portions.

Like the structural portions, said pins 14 and bushing 15 are provided outside the area focused by the FOV, always with the aim of minimizing the generation of artefacts.

The fixing system allows to reduce to a minimum the mechanical parts for the fixing (no screws or blocking systems). Thanks to the weight of the patient, the fixing system allows to obtain a good blocking system, easy and fast to fix/remove without the use of tools. A human operator inserts or removes said pins 14 into or from said bushings 15; with a slight pressure the device 4 becomes integral with the gurney 6.

Figure 4:
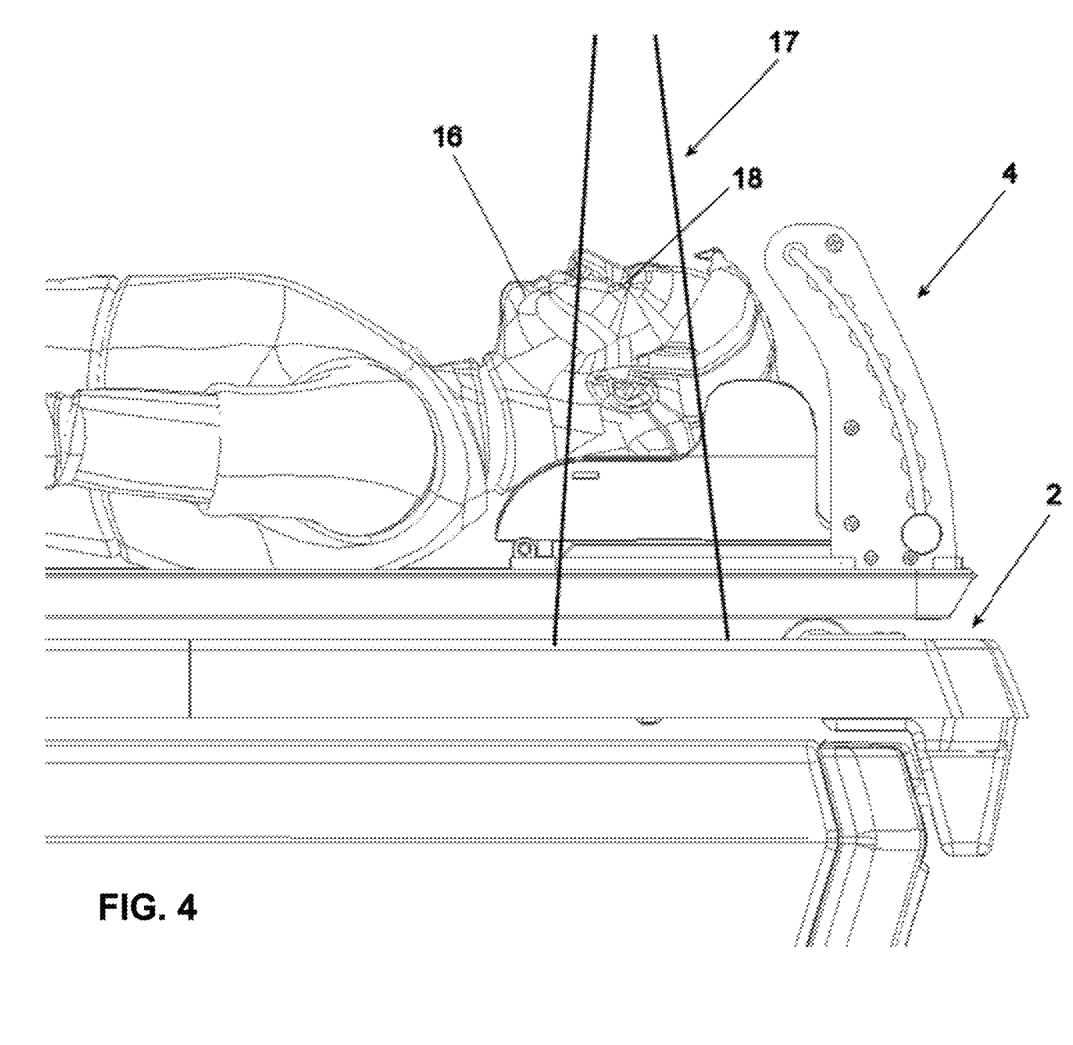
FIG. 4 is a lateral view of a patient having her/his head parallel to the gurney.

FIG. 4 shows a detail of an acquisition of the head 16 of a patient, of whom the ear has to be acquired. If her/his head is kept at 0° with respect to the gurney 6 (i.e. the head is co-planar to the gurney), an X-ray beam 17 impinges on both the eyes 18 and the pituitary gland (not shown) of the patient, with ensuing useless irradiation of organs which are particularly sensitive to X-rays, without acquiring portions that are useful for the investigation under way.

Figure 5:
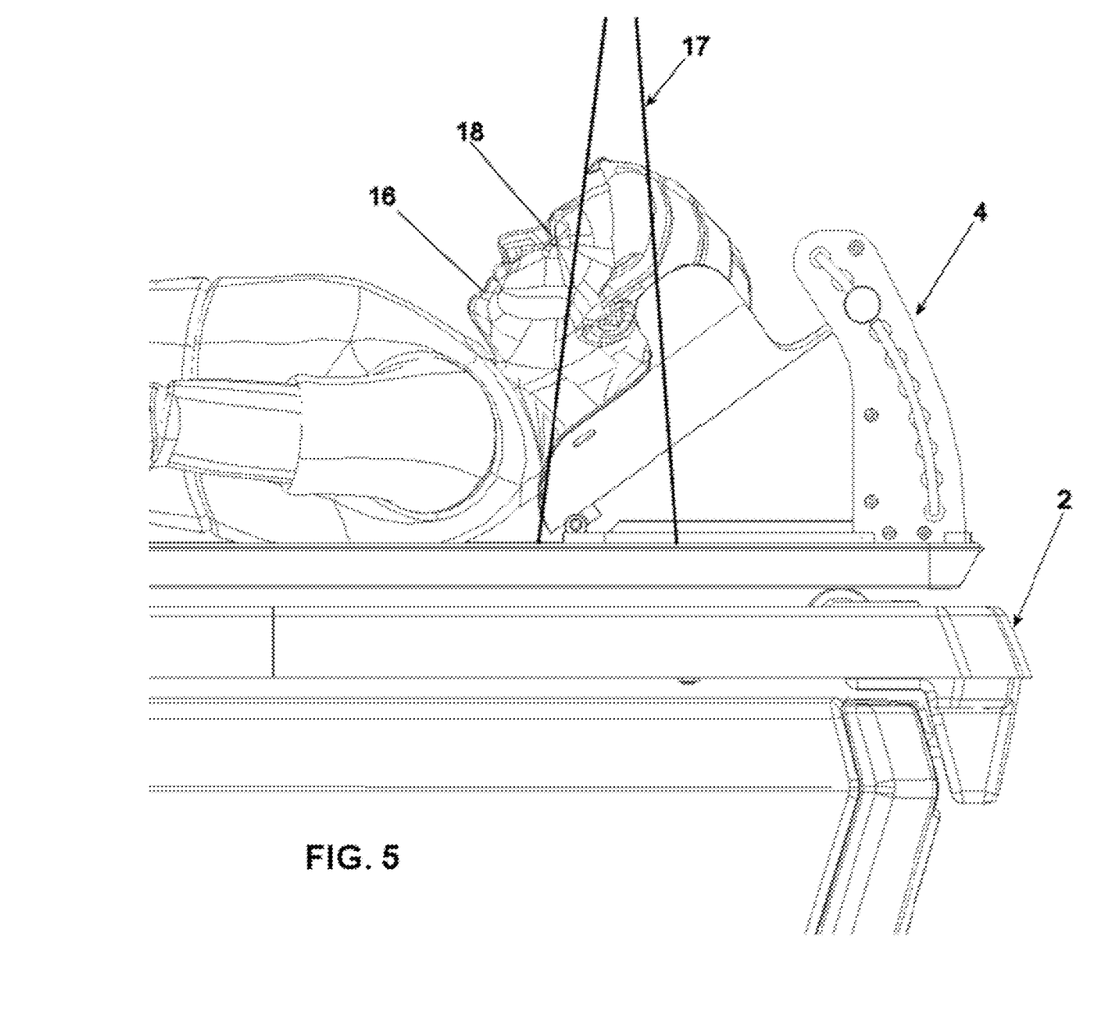
FIG. 5 is a lateral view of a patient having her/his head tilted with respect to the gurney.

FIG. 5 shows a detail of the acquisition of the head 16 of a patient of whom the ear has to be acquired. If her/his head is kept at 45° with respect to the gurney 6 (i.e. tilted with respect to the gurney), the X-ray beam 17 irradiates the ear area only, without impinging on the eyes 18 nor the pituitary gland (not shown) of the patient.

It is worth noting that to said dome 7 special cushions, wedges and removable bands (not shown) can be added, aiming at further immobilizing the patient's head; such devices are known in the art. Said protuberances 27 are provided for fixing said further blocking elements.

Moreover, FIG. 1 shows three double arrows (X, Y, and Z) showing the movement of a gurney 6 in the three space axes. The longitudinal axis Y is the direction for extracting the gurney out of the gantry 3 or inserting the gurney inside the gantry 3; the lateral axis X (right/left) allows the movement of the gurney in a direction orthogonal to the longitudinal direction; while the vertical axis Z allows the raising/lowering of said gurney with respect to the floor plane.

Said patient support 2 comprises a base 71 lying on the floor and integral to said gantry 3; and a gurney 6 mobile with respect to the floor. The patient lays on said gurney 6. Optionally the adjustable device 4 is provided for immobilizing the patient's head, which is fixed to said gurney 6.

Figure 6:
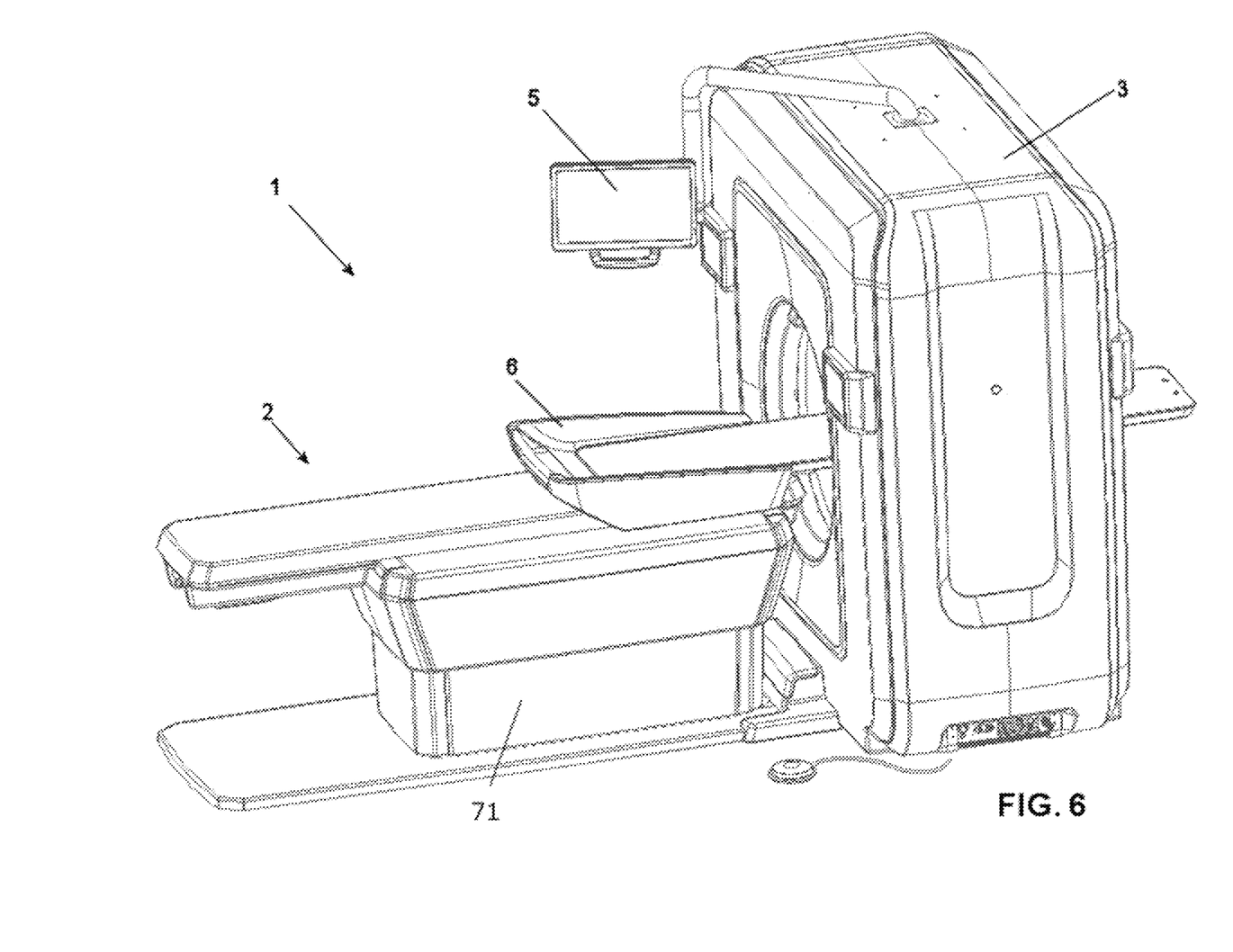
FIG. 6 is an axonometric view of the radiographic apparatus according to the present invention, with the gurney in its end of stroke inserted position (second extreme position)

FIG. 6 shows the same elements shown in FIG. 1.

In FIGS. 1 and 6, the gurney 6 is shown in its two extreme positions: in FIG. 1, the gurney 6 is shown in its completely extracted position, while in FIG. 6 the gurney 6 is shown in its position inserted in the gantry 3 up to its end of stroke. The comparison between FIG. 1 and FIG. 6 shows the longitudinal movement along the Y axis of the gurney 6 itself, sliding inside the through hole 103 of the gantry.

Figure 7:
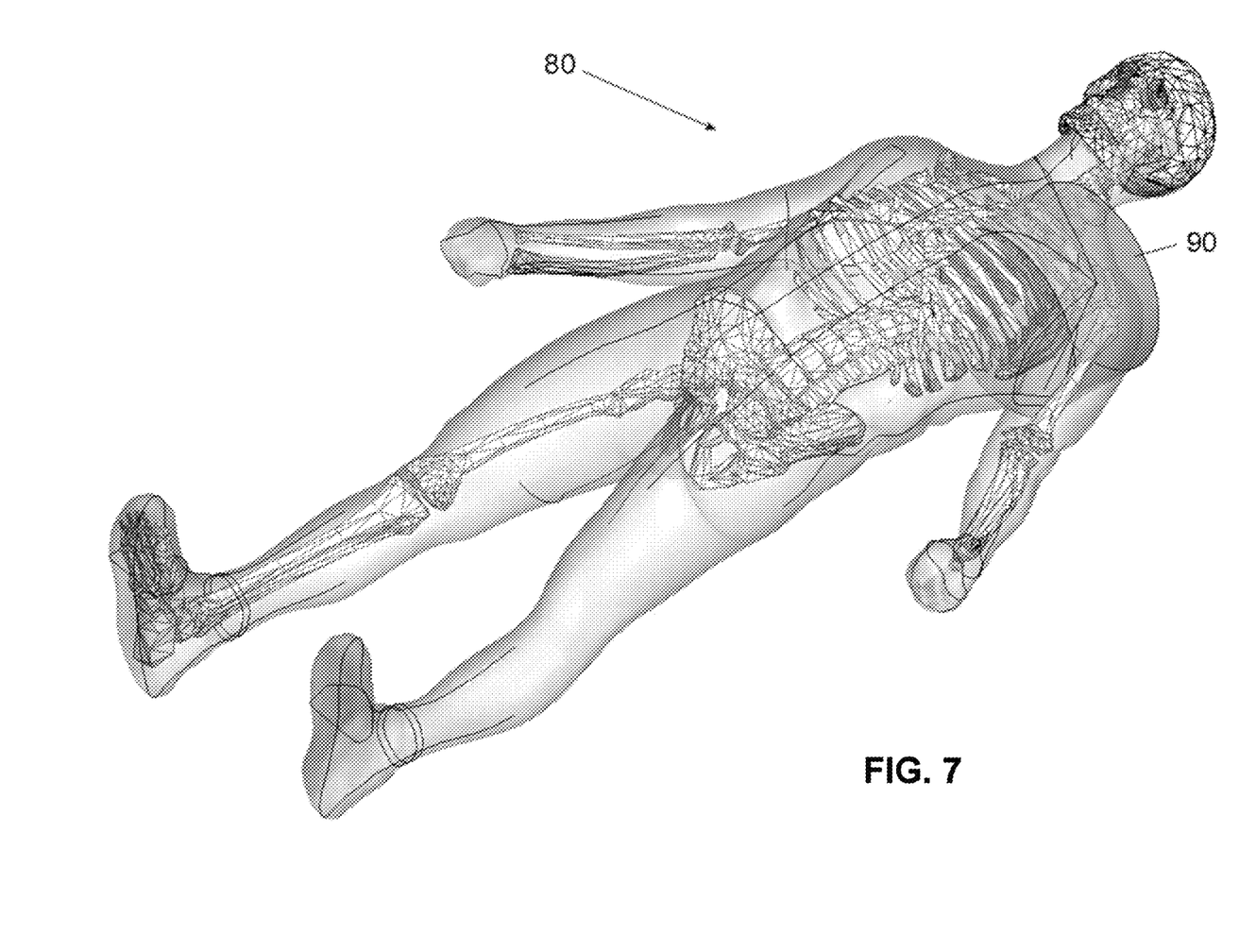
FIG. 7 is a schematic view of a patient; his left shoulder is under acquisition.
Figure 8:
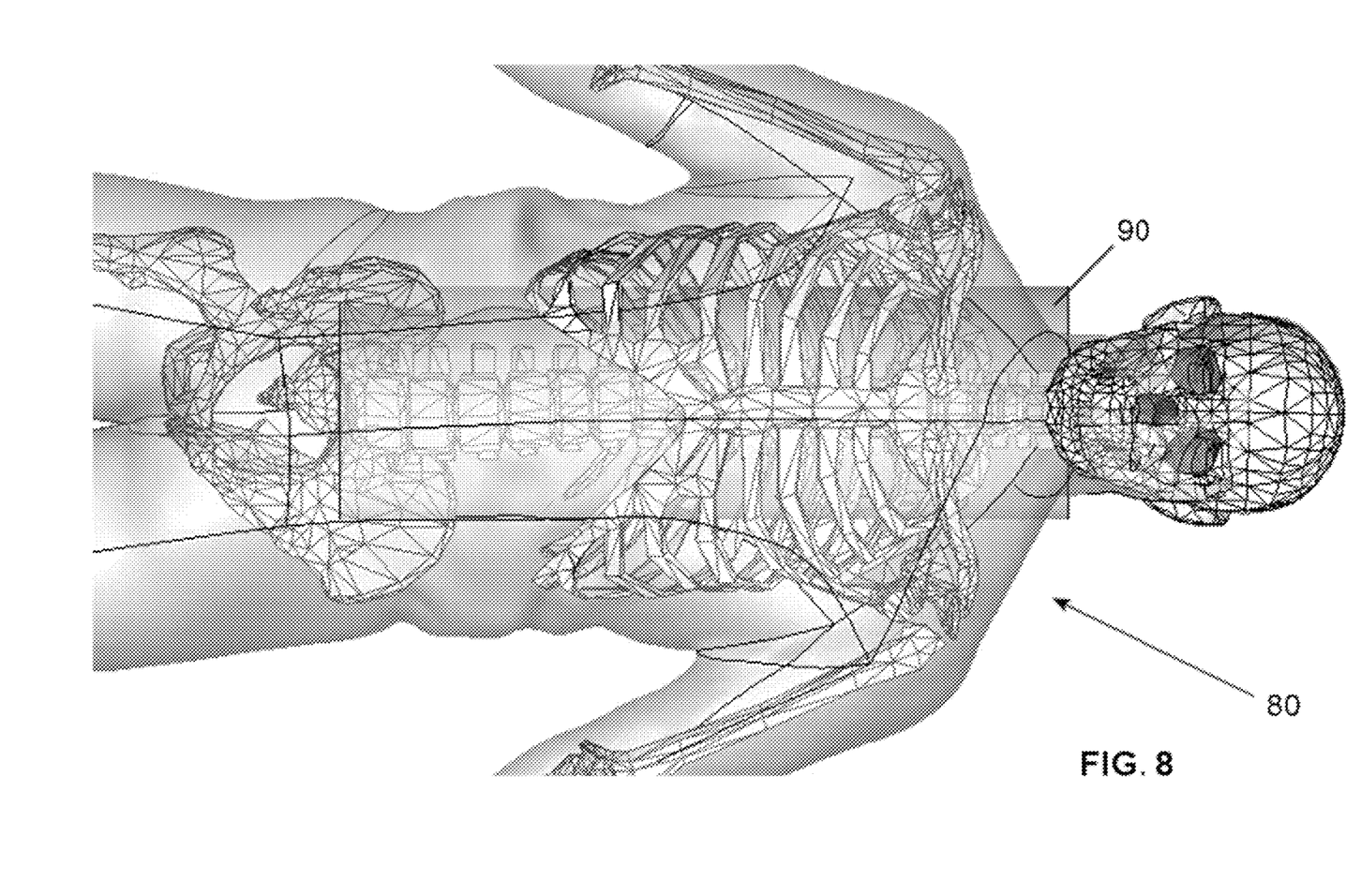
FIG. 8 is a schematic view of a patient; his vertebral column is under acquisition.

FIG. 7 and FIG. 8 show the advantages of the present invention.

FIG. 7 shows an area 90 to be acquired consisting in the left shoulder of a patient 80 lying on the gurney 6, which in this case is translated laterally (along the X axis) of about 20 cm with respect to the gurney centered position with respect to the through hole 103 of said gantry.

It is worth noting that the FOV is always generated in a way concentric to the rotation axis of the X-ray source-detector system, independently of the diameter of the volume to be acquired. Therefore, the said FOV is co-axial to the through hole 103 of said gantry 3.

According to the present invention, just the area 90 to be acquired indicated in grey in the image is irradiated, therefore saving the adjacent anatomical structures.

Instead, in a spiral CT radiographic apparatus, this is not possible. In order to focus offset fields of view, big X-ray sensor panels are used, irradiating patient's portions that are not to be acquired. In the example of FIG. 7, both shoulders of the patient 80 would be irradiated and acquired, administering a partially useless X-ray dose to said patient.

On the other hand, FIG. 8 shows the principle of multiple acquisitions. The applicant filed the application EP2868275A1, teaching to perform a stitching procedure of radiographic images acquired in at least two sub-acquisitions of smaller volumes, which are then summed so as to acquire a bigger radiograph.

In the example of FIG. 8, multiple sub-acquisitions were summed, by translating said gurney 6 in the longitudinal direction for a number of times equal to the length of the anatomical portion to be acquired divided by the 17 cm of the FOV height. In practice, in order to acquire the vertebral column of an adult patient in its entirety, at least four-five successive sub-acquisitions are necessary, which are then summed post-acquisition.

The lateral movement (right/left) of said gurney 6 is obtained by implementing a motoreducer system with a rack-and-pinion transmission, so as to actuate a cart on which the gurney is fixed. Said mechanical system, laying outside the irradiated area, does not require special cautions to improve the radiotransparency of the components.

In practice, the patient lays on the gurney 6 and is inserted into the gantry 3, roughly centering the desired anatomic area through laser indicators. Then some scout images are acquired (typically a frontal and a lateral image), allowing to understand whether the desired anatomical area is correctly focused inside said FOV. According to said scout images the fine centering of the patient is performed, making small, even remote, adjustments in the three space axes (X, Y and Z), without the need to repeat the scout acquisitions. Then the real acquisition/s can take place.

REFERENCE NUMBERS

1 Extraoral radiographic apparatus
2 Table
3 Gantry
4 Device for immobilizing patient's head
5 Screen
6 Gurney
7 Headrest dome
8 Basal plate
9 Junction
10 Upright
11 Slit
12 Cursor
13 Nut
14 Pin
15 Bushing
16 Head
17 X-ray beam
18 Eyes
27 Protuberance
71 Base
80 Patient
90 Area to be acquired
103 Gantry passing hole

The invention claimed is:

1. A radiographic apparatus comprising a gantry and a table for supporting a patient, the table comprising a device configured to immobilize a head of the patient lying on the table,
wherein the device configured to immobilize a head of the patient comprises:
a dome configured to support the head of the patient therein;
a basal plate;
at least one junction provided at a first end of the basal plate;
two uprights provided at a second end of the basal plate opposed to the first end, two slits being defined in the two uprights, a slide being disposed within each slit; and
a cursor sliding in the two slits and configured to be blocked in position by a bushing, and
wherein the basal plate, the at least one junction, the two uprights, the cursor, and the bushing are all radio-transparent and non-metallic.

2. The radiographic apparatus according to claim 1, wherein the device configured to immobilize the head of the patient is provided with a coupling and releasing system to the table, the coupling and releasing system comprising a plurality of pins disposed under the basal plate, a plurality of bushings being provided on the table at mating points, so as to enable an insertion of the plurality of pins into the plurality of bushings with hand pressure.

3. The radiographic apparatus according to claim 1, wherein the sliding of the cursor the two slits provides for a tilting of the dome around the at least one junction, between two positions:
a first extreme position wherein the dome is parallel to the table; and
a second extreme position wherein the dome is tilted 45° with respect to the table.

4. The radiographic apparatus according to claim 3, wherein the cursor is adapted to stop at pre-set intermediate positions between the first and the second extreme positions.

5. The radiographic apparatus according to claim 3, wherein the cursor is adapted to stop at any intermediate position between the first and the second extreme positions.

6. The radiographic apparatus according to claim 1, wherein the dome comprises a plurality of protuberances protruding from a border of the dome at a distal end proximal tod the two uprights.

7. The radiographic apparatus according to claim 1, further comprising members coupled to the dome to immobilize the patient, the members being selected from the group consisting of a removable cushion, a wedge, and a band.

8. The radiographic apparatus according to claim 1, wherein the gantry is provided with a through hole, an X-ray source, and a sensor panel, the table comprising a gurney movably being mounted on a base in relation to the gantry with at least one degree of freedom, and wherein the gurney is movably supported along three spatial axes so as to acquire the patient's anatomical area of interest, a field of view being always concentric to the through hole of the gantry.

9. The radiographic apparatus according to claim 8, wherein positioning the gurney (6) supporting the patient (80) occurs in two successive steps:
(a) a first rough positioning through laser indicators; and
(b) a second fine positioning through scout acquisitions; patient positioning occurring due to a moving of the gurney in the three spatial axes.

10. The radiographic apparatus according to claim 8, wherein the radiographic apparatus is configured to provide a radiograph having dimensions bigger than dimensions of the sensor panel by performing at least two sub-acquisitions which are then summed with a stitching procedure of the at least two sub-acquisitions; the gurney being re-positioned between a first sub-acquisition and a following sub-acquisition, so as to cover an entirety of the anatomical area of interest.

11. The radiographic apparatus according to claim 8, wherein a movement of the gurney along the a first one of the three spatial axes occurs through a moto-reducer system with a rack-and-pinion transmission, so as to actuate a cart on which the gurney is fixed.

12. The radiographic apparatus according to claim 8, wherein the gurney is provided with:
a longitudinal stroke of 150 cm;
a lateral stroke up to 21 cm; and
a height stroke of about 40 cm.

13. The radiographic apparatus according to claim 1,
wherein the gantry is provided with a through hole, an X-ray source, and a sensor panel; and
further comprising a patient support comprising a gurney movably mounted on a base in relation to the gantry, the gurney being movable with at least one degree of freedom,
wherein the gurney is movably supported along three spatial axes to acquire an anatomical area of interest of a patient, a field of view being always concentric to the through hole of the gantry.

14. A method of positioning a patient in a radiographic apparatus according to claim 8, wherein the positioning of the patient comprises:
positioning the gurney supporting the patient in two successive steps:

(a) a first rough positioning through laser indicators, and
(b) a second fine positioning through scout acquisitions;
wherein the positioning of the patient is achieved by moving the gurney along the three spatial axes.

15. The method according to claim 14, further comprising:
acquiring a radiograph with dimensions larger than dimensions of the sensor panel by performing at least a first and a second sub-acquisition, which are then summed using a stitching procedure of the first and the second sub-acquisitions, the gurney being re-positioned between the first sub-acquisition and the second sub-acquisition, so as to cover an entirety of the anatomical area of interest.

\* \* \* \* \*